(12) United States Patent
Hodgkinson

(10) Patent No.: US 7,091,487 B2
(45) Date of Patent: Aug. 15, 2006

(54) NON-DISPERSIVE IR MEASUREMENT OF GASES USING AN OPTICAL FILTER

(75) Inventor: Elizabeth Jane Hodgkinson, Loughborough (GB)

(73) Assignee: Lattice Intellectual Property Limited, London (GB)

( * ) Notice: Subject to any disclaimer, the term of this patent is extended or adjusted under 35 U.S.C. 154(b) by 99 days.

(21) Appl. No.: 10/296,198

(22) PCT Filed: May 30, 2001

(86) PCT No.: PCT/GB01/02377

§ 371 (c)(1),
(2), (4) Date: May 6, 2003

(87) PCT Pub. No.: WO01/94916

PCT Pub. Date: Dec. 13, 2001

(65) Prior Publication Data
US 2003/0183766 A1    Oct. 2, 2003

(30) Foreign Application Priority Data
Jun. 2, 2000 (GB) ................................ 0013409.8
Sep. 13, 2000 (GB) ................................ 0022427.9

(51) Int. Cl.
*G01N 21/35* (2006.01)
(52) U.S. Cl. .................. 250/343; 250/339.12
(58) Field of Classification Search .......... 250/343, 250/344, 339.12, 339.13, 341.1, 341.5; 356/434, 356/437; 99/331
See application file for complete search history.

(56) References Cited

U.S. PATENT DOCUMENTS

| 4,323,777 | A | | 4/1982 | Baskins et al. |
| 4,560,875 | A | | 12/1985 | Crowder |
| 4,567,366 | A | | 1/1986 | Shinohara |
| 5,060,572 | A | * | 10/1991 | Waizmann ................ 101/424.1 |
| 5,555,885 | A | | 9/1996 | Chance |
| 5,818,598 | A | * | 10/1998 | Kebabian ..................... 356/434 |
| 5,822,058 | A | * | 10/1998 | Adler-Golden et al. ..... 356/303 |
| 5,854,681 | A | | 12/1998 | Delignieres et al. |
| 5,894,128 | A | * | 4/1999 | Nakamori .................... 250/343 |
| 5,983,120 | A | | 11/1999 | Groner et al. |
| 6,037,592 | A | | 3/2000 | Sunshine et al. |
| 6,155,160 | A | * | 12/2000 | Hochbrueckner ............ 99/331 |

(Continued)

FOREIGN PATENT DOCUMENTS

EP        0 616 207        9/1994

(Continued)

OTHER PUBLICATIONS

NDC Infrared Engineering: "Narrow Bandpass Filters type NBP", 2000, http://www.ndc.com/products/newtfod/narrow/narrow.html.

(Continued)

*Primary Examiner*—Otilia Gabor
(74) *Attorney, Agent, or Firm*—Oblon, Spivak, McClelland, Maier & Neustadt, P.C.

(57) ABSTRACT

A method and apparatus for determining the safety of a gas mixture containing flammable components such as methane together with ethane or other hydrocarbon, together with a diluent gas. The method includes the filtered infrared spectroscopy of the gas mixture in a gas cell using a filter. The peak transmission wavelength and bandwidth of the filter are so chosen to provide an output, when an infrared light source having a flat wavelength distribution is used, indicative of the % LEL of the gas mixture, within a predetermined tolerance. The filter may be a gas correlation filter containing a mixture of methane and ethane, together with a diluent gas.

19 Claims, 4 Drawing Sheets

U.S. PATENT DOCUMENTS 6,435,003 B1 * 8/2002 Warburton .................. 73/23.2
6,545,278 B1 * 4/2003 Mottier et al. ......... 250/339.13

FOREIGN PATENT DOCUMENTS

| EP | 0 931 496 | 7/1999 |
| GB | 2 176 889 | 1/1987 |
| JP | 59-212738 | 12/1984 |
| JP | 62-273436 | 11/1987 |
| JP | 9-500304 | 1/1997 |
| JP | 10-507838 | 7/1998 |
| JP | 11-500648 | 1/1999 |
| JP | 11-118712 | 4/1999 |
| WO | 99 197 12 | 4/1999 |
| WO | 99 19712 | 4/1999 |

OTHER PUBLICATIONS

H. I. Coward et al, Limits of Flammability of Gases and Vapours, Pub. 1952, National Bureau of Mines Bulletin 5C3, pp. 5-9.

* cited by examiner

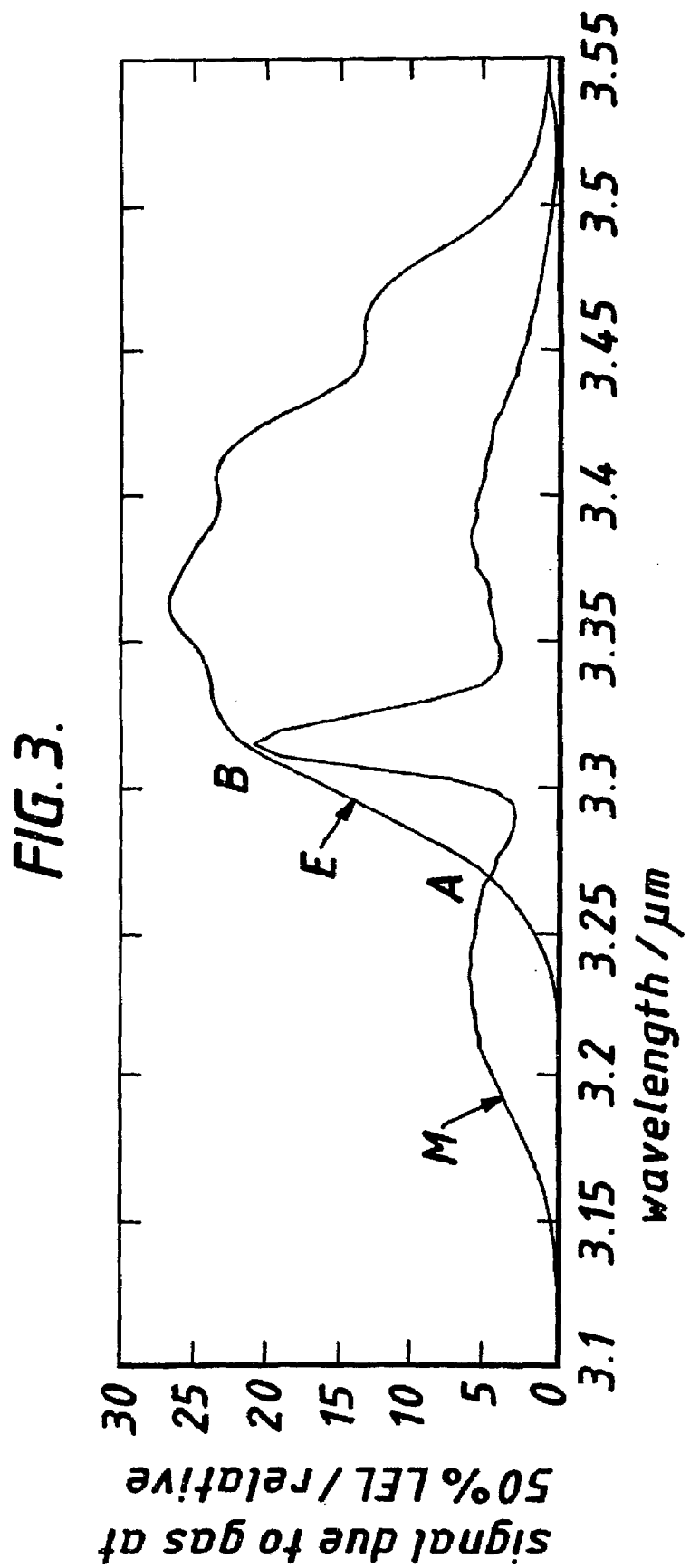

NON-DISPERSIVE IR MEASUREMENT OF GASES USING AN OPTICAL FILTER

FIELD OF THE INVENTION

The present invention relates to various aspects of determining the safety of a gas mixture which contains flammable components by infrared spectroscopy, especially but not exclusively where the gas mixture contains methane and ethane in unknown proportions.

BACKGROUND OF THE INVENTION

Flammable gas concentration measurements are made in a number of safety-critical situations. One such flammable gas is natural gas, which typically comprises mainly methane, plus higher hydrocarbons, inert gases and trace components. Natural gas detectors are needed for a number of applications including response to public reported gas escapes and for continuous monitoring of plant/equipment using permanently installed detectors. They are required to measure the gas concentration as a percentage of the lower explosion limit (LEL) of the gas mixture, this being an important safety parameter.

The concentration of a flammable gas component, such as methane, in a gas mixture can, theoretically, be measured by infrared spectroscopy, using a filter having a peak transmission wavelength equal to one of the wavelengths of absorption by methane, e.g. at 3.32 μm. The filter and the light source together define a selected range of wavelengths over which the spectral measurement of the gas mixture is made, giving a degree of selectivity for individual gas species. The measured concentration can be converted into % LEL to give an indication of the safety of the gas mixture. However, gas mixtures from natural sources will usually contain unknown proportions of other flammable components, such as hydrocarbons including ethane, propane and butane, while in some cases such components are deliberately added. The presence of these additional flammable components disturbs the accuracy of the % LEL measurement, by absorbing infrared radiation to a degree which is out of proportion with their influence on LEL, relative to methane.

SUMMARY OF THE INVENTION

It is an object of the present invention to provide a filter for use in the infrared spectroscopy of a gas mixture, which enables a more accurate indication of % LEL to be achieved.

We have discovered that not only the peak transmission wavelength of the filter, but also its band width are important and that improved accuracy can be achieved by suitable selection of these factors.

Thus, according to a first aspect of the invention, there is provided a method for determining the safety of a gas mixture containing first and second flammable components, together with a diluent gas, comprising the filtered infrared spectroscopy of the gas mixture using a filter, the peak transmission wavelength ($\lambda_{max}$) and bandwidth of which are so chosen to provide an output indicative of the % LEL of the gas mixture, within a predetermined tolerance.

The invention is particularly advantageous where the two flammable components exhibit some absorption of infrared in the same region of the spectrum. Typical examples are components having a some chemical similarity, such as members of the same chemical series. Thus, the first flammable component will typically be methane and the second flammable component will be ethane, propane or a mixture thereof. When the first component is methane, the invention is less successful where the second component is hydrogen.

The diluent components present in the gas mixture will in practise usually be air, i.e. nitrogen, oxygen, carbon dioxide, water vapour and inert gases, but the invention is applicable to gas mixtures where the diluent components do not have a significant infrared absorption close to the peak transmission wavelength of the filter. Gas components which do have a significant infrared absorption close to the peak transmission wavelength of the filter will disturb the measurement and are therefore preferably avoided.

The filter is preferably so chosen that the output is indicative of the % LEL for the mixture, within a tolerance of ±3%.

We have found that this accuracy can be achieved by the application of certain criteria to the selection of the filter.

Firstly, we have found that it is preferred that the peak transmission wavelength and the band width of the filter are so chosen that, when viewed through said filter, the intensity of transmission ($I_1$) through a gas mixture containing 50% LEL of said first component is equal to the intensity of transmission ($I_2$) through a gas mixture containing 50% LEL of said second component, within a tolerance of 30%, preferably within 20%, ideally within 10%. For mixtures of methane and ethane in air, $$I_{methane} \approx I_{ethane}$$

occurs, depending upon the band width, at wavelengths of about 3.27 μm and about 3.32 μm in the mid infrared region, and at wavelengths of about 1.67 μm in the near infrared region.

A second preferred criterion is that, at the peak transmission wavelength of the filter, the rate of change of intensity with increasing wavelength ($\delta I_1/\delta \lambda$) for the gas mixture containing 50% LEL of said first component is equal to the rate of change of intensity with increasing wavelength ($\delta I_2/\delta \lambda$) for the gas mixture containing 50% LEL of said second component, within a tolerance of 100 I/μm, preferably within 10 I/μm. For mixtures of methane and ethane in air we have found that $$\delta I_{methane}/\delta \lambda \approx \delta I_{ethane}/\delta \lambda$$

and that $$I_{methane} = I_{ethane}$$

occurs at a wavelength of about 3.32 μm and a band width, expressed in terms of full width at half maximum, of less than 0.7% $\lambda_{max}$.

Thus, in the mid infrared region we prefer that the filter has a peak transmission wavelength $\lambda_{max}$ of (i) from 3.263 to 3.271 μm, most preferably from 3.265 to 3.269 μm, with a bandwidth of between 0.8% and 1%, or (ii) between 3.31 and 3.32 μm, with a bandwidth of less than 0.7%. In the near infrared region we prefer that the filter has a peak transmission wavelength $\lambda_{max}$ of from 1.67 to 1.68 μm, most preferably from 1.673 to 1.675 μm, with a bandwidth of between 0.5% and 6%.

A filter having $\lambda_{max}$=3.27 μm and a band width of 0.9% $\lambda_{max}$ is commercially available from NDC Infrared Engineering of Galliford Road, Malden, Essex, UK. The same manufacturers can also provide a filter having $\lambda_{max}$=1.67 μm and a band width of 0.9% $\lambda_{max}$. More preferred filters can be manufactured with suitable adjustments to known processing techniques, or by selection from a variety of filters, to provide a product with the desired characteristics.

It is indeed surprising that, in the mid infrared region, reducing the band width of the filter improves the accuracy of the % LEL measurement, since reducing the band width significantly reduces signal strength. It is also surprising that moving $\lambda_{max}$ to a position where $I_{methanae}$ and $I_{ethanae}$ are substantially equal, at a band width of less than 0.7% $\lambda_{max}$, improves the accuracy of the % LEL measurement.

The invention provides the advantage that the preferred filter characteristics are independent of relative proportions of gases in the gas mixture to be examined.

According to a second aspect, the invention provides an apparatus for determining the safety of a gas mixture containing first and second flammable components, together with a diluent gas, the apparatus comprising a region for receiving gas to be examined, an infrared light source positioned to direct infrared light through said region, a sensor for measuring the intensity of light passed through said region and a filter, positioned in the light path between the source and the sensor, characterised in that the peak transmission wavelength ($\lambda_{max}$) and bandwidth of the filter are so chosen to provide the sensor with an output indicative of the % LEL of the gas mixture, within the predetermined tolerance.

The region for receiving gas to be examined may be provided by a gas cell for containing a sample of such gas, or be provided by an open optical path through which gas to be examined can flow.

The invention also provides a filter for use in the infrared spectroscopy of a gas mixture containing methane as a first component and a second component selected from ethane, propane and mixtures thereof, together with a diluent gas, characterised in that the peak transmission wavelength ($\lambda_{max}$) and bandwidth of the filter is such as to provide an output, when an infrared light source having a flat wavelength distribution is used, indicative of the % LEL of the gas mixture, within a predetermined tolerance.

The nature of the infrared light source is a secondary consideration. In theory, if the light source has a "white" output, that is a flat wavelength distribution in that part of the spectrum being examined, then it has no effect upon the preferred characteristics of the filter. However, in practice, the infrared light source may not have a flat distribution, particularly if an LED is used as the light source. In this event, it is preferred to select the filter characteristics with the characteristics of the infrared light source in mind. Similar considerations also apply to the sensor.

Thus, also provided by the invention is the combination of an infrared light source and a filter for use in the infrared spectroscopy of a gas mixture containing methane as a first component and a second component selected from ethane, propane and mixtures thereof, together with a diluent gas, characterised in that the peak transmission wavelength ($\lambda_{max}$) and bandwidth of the filter is such as to provide an output, when the light source is used, indicative of the % LEL of the gas mixture, within the predetermined tolerance.

While interference filters are suitable for use in the invention, a gas correlation filter may alternatively be used.

Thus, in an alternative embodiment, the filter comprises a gas correlation filter containing a known mixture of the first and second flammable components, together with a diluent gas.

The invention still further provides a gas correlation filter for use in the infrared spectroscopy of a natural gas, the filter containing a mixture of methane and a second flammable component selected from ethane, propane and mixtures thereof, together with a diluent gas.

The invention will now be illustrated, purely by way of example, by reference to the accompanying drawings, in which.

Figure 4B:
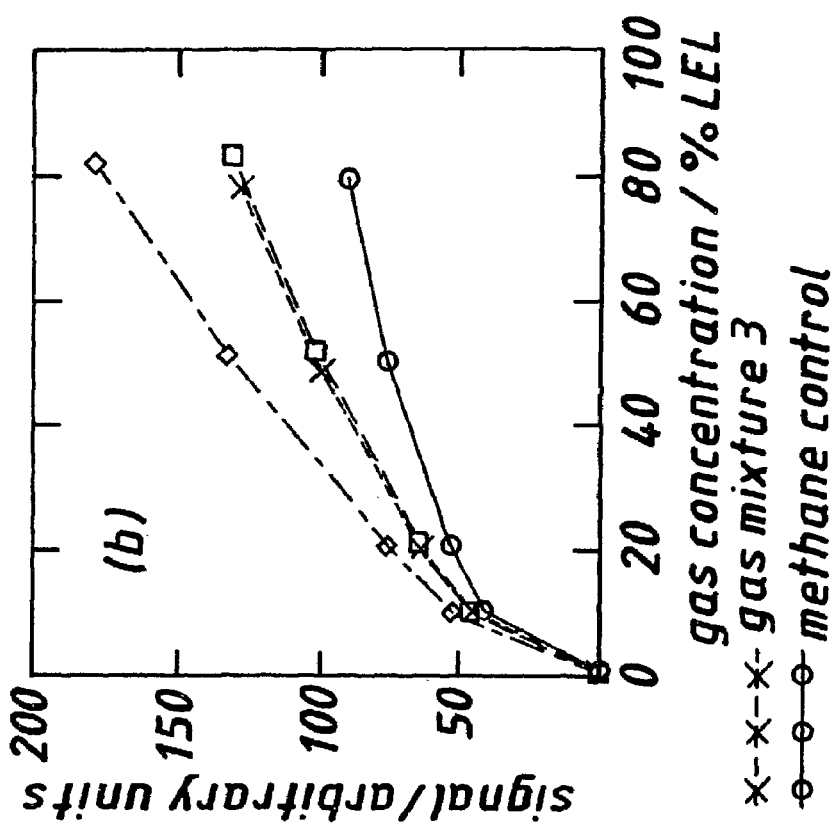
Figure 4A:
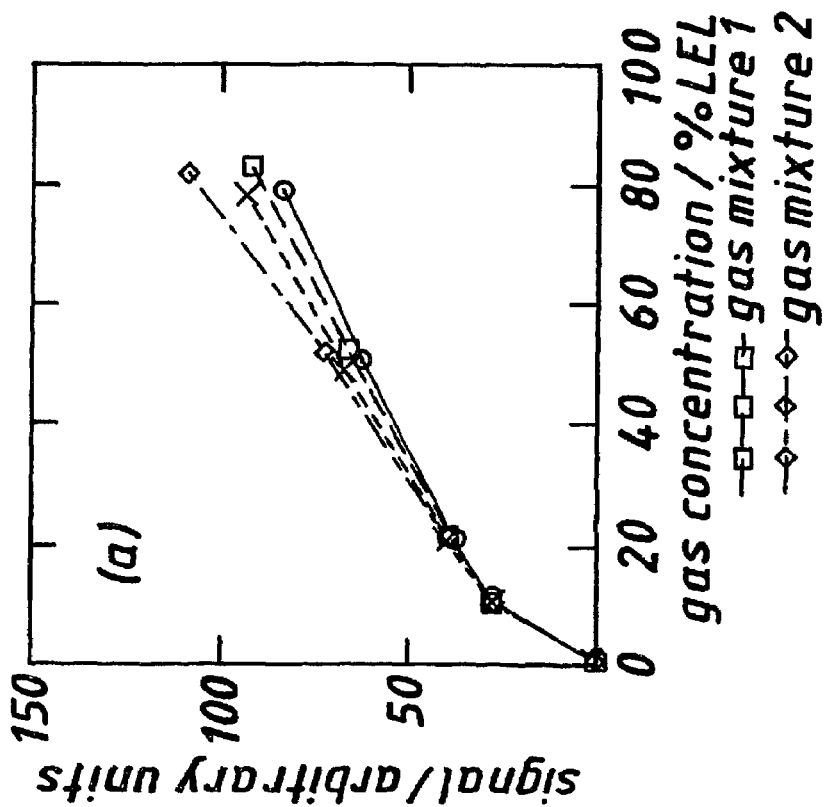

FIG. 3 is a simulation graph showing the output signal at 50% LEL for methane and ethane using a mid infrared filter with a band width of 0.6% $\lambda_{max}$; and FIGS. 4a and 4b show actual experimental results obtained using an interference filter with peak transmission at 3.266 μμm and an interference filter with peak transmission at 3.324 μm, respectively, to measure the concentration of various gas mixtures on the % LEL scale.

Figure 1:
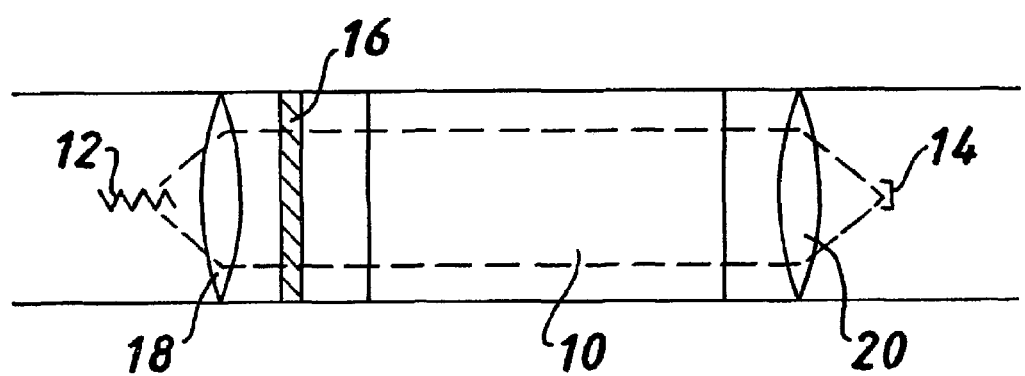
FIG. 1 is a schematic representation of an apparatus for determining the safety of a gas mixture.

Referring to FIG. 1, there is shown an apparatus for determining the safety of a gas mixture containing first and second flammable components, together with a diluent gas. The apparatus comprises a region for receiving gas to be examined provided by a gas cell 10 for containing such a sample of gas. An infrared light source 12 is positioned to direct infrared light through the gas sample in the cell 10. A suitable infrared light source is Chemled LED 33, ex Telecom Devices Corporation, available through Access Pacific Ltd, Wellingborough, Northants, UK. A sensor 14 is provided for measuring the intensity of light passed through the gas sample in the cell. A suitable sensor is P791-11 PbSe photodetector ex Hamamatsu Photonics UK Ltd, Enfield, UK. A filter 16 is positioned between the IR light source 12 and the cell 10, but may in an alternative configuration be positioned between the cell 10 and the sensor 14. Lenses 18 and 20 are provided to ensure that the light from the source 12 is focussed onto the sensor 14. Selection of a near infrared light source and detector, together with the near infrared filters described above, would also result in an acceptable apparatus.

Figure 2:
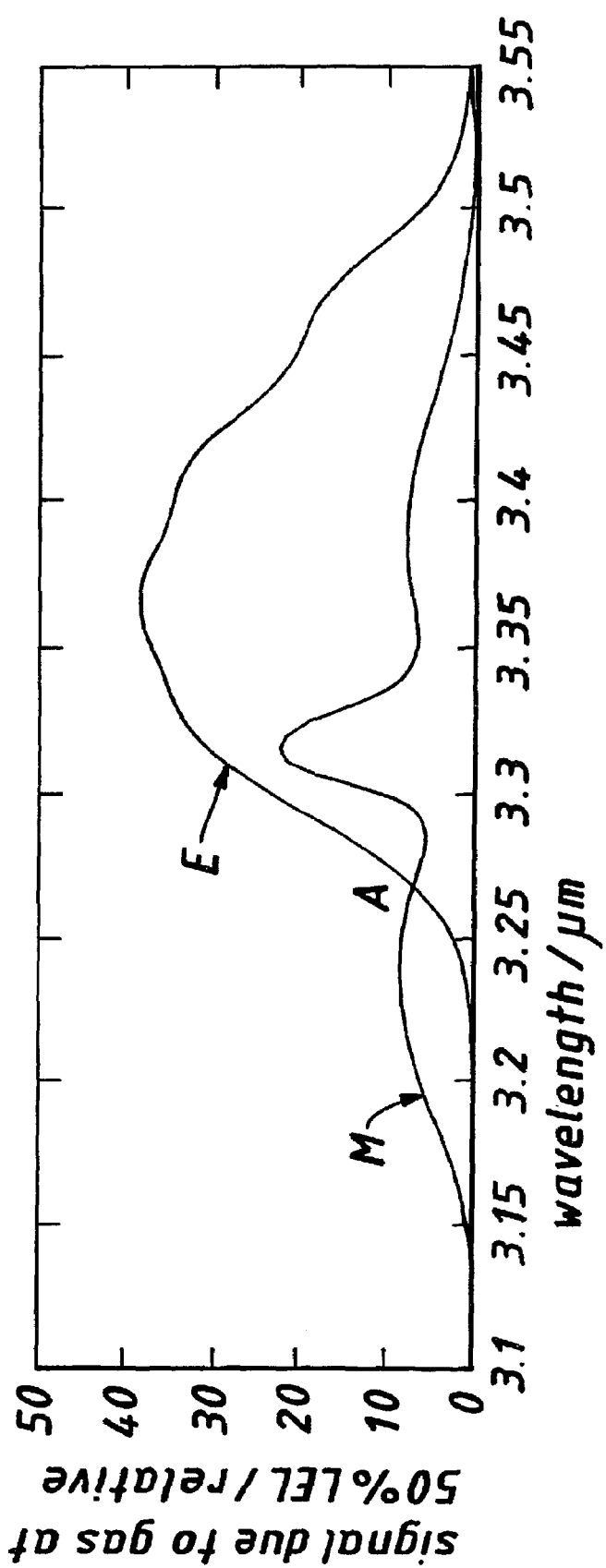
FIG. 2 is a simulation graph showing the output signal at 50% LEL for methane and ethane using a mid infrared filter with a band width of 0.9% $\lambda_{max}$.

Referring to FIG. 2, it can be seen that between the wavelengths of 3.1 μm and 3.55 μm, the absorption spectra of methane (line M) and ethane (line E) are very different. However, they are found to cross at point A, at a wavelength of about 3.267 μm. This Figure indicates preferred characteristics for the filter, namely a peak transmission wavelength of about 3.267 μm. However, at this wavelength, the slope of each line is not similar, i.e. the rate of change of intensity with increasing wavelength for the two gases is different. This does not therefore indicate the most preferred characteristics for the filter, for which reference should be made to FIG. 3. However, close examination of the slopes of the lines at point A, will indicate that a band width of 0.9% $\lambda_{max}$ or less will lead to an error in the measurement of % LEL for a 90/10 methane/ethane mixture of no more than 3%.

Referring to FIG. 3, where the band width of the filter is reduced to 0.6%, it can be seen that there is now a second region B in which the lines M and E are close to each other. This is at a wavelength of about 3.32 μm. Furthermore, at this wavelength, the slope of each line is similar, i.e. the rate of change of intensity with increasing wavelength for the two gases is substantially equal. This Figure indicates the most preferred characteristics for the filter, namely a peak transmission wavelength of about 3.315 μm and a band width of about 0.6% $\lambda_{max}$.

It can also be seen from FIG. 3, that the overall signal strength is reduced, compared to FIG. 2.

EXPERIMENTAL EXAMPLE

Experiments will now be described that confirm the practical application of the previous simulation analysis. By way of example, experiments were conducted using the mid infrared filters described above, but the principle is equally applicable to near infrared operation.

A laboratory FTIR spectrometer (Biorad FTS-60A) was used to demonstrate the benefit of choosing filters referred to above. The concentration of a series of test gas mixtures was established using two interference filters, the mixtures being indicative of natural gas compositions found in the UK. The test gas mixtures had the compositions given in Table 1.

TABLE 1

Compositions in mol % of three artificial gas mixtures typical of natural gas. LELs have been calculated according to the method given by Coward and Jones using LELs of individual components from BS EN 50054:1991. (Reference: H F Coward and G W Jones. Limits of flammability of gases and vapours. National Bureau of Mines, Bulletin 503 [1952])

| Gas component | Composition 1 | Composition 2 | Composition 3 |
|---|---|---|---|
| Nitrogen | 1.72 | 0.731 | 2.21 |
| Carbon dioxide | 0.32 | 2.11 | 0.8 |
| Methane | 93.55 | 86.48 | 92.86 |
| ethane | 3.27 | 7.47 | 3.02 |
| propane | 0.763 | 2.5 | 0.635 |
| i-butane | 0.122 | 0.182 | 0.131 |
| n-butane | 0.153 | 0.392 | 0.156 |
| n-pentane | 0.103 | 0.13 | 0.18 |
| C6+ | 0 | 0.0003 | 0.0002 |
| LEL/% vol | 4.89% vol | 4.63% vol | 4.94% vol |

The natural gases at 100% were blended with hydrocarbon free air in varying proportions. The concentration was determined using a methane analyser (ADC dual Luft cell), which was separately adjusted for the cross-sensitivity to the other components of each gas mixture to give an accurate reading for each.

Gas spectra were measured using a 10 cm pathlength gas cell in a laboratory FTIR spectrometer. Spectra were measured in the mid infrared (centred around 3.3 µm). The spectrometer (Bio-Rad FTS-60A) was set up according to the manufacturer's instructions, for high resolution mid infrared spectroscopy. A high temperature ceramic light source was used, with a wide band KBr beamsplitter and liquid nitrogen cooled MCT detector, all of these being supplied with the spectrometer. KBr windows were also used in the gas cell. The highest available resolution (0.25 cm$^{-1}$) was chosen.

Spectra from the sample gases were corrected for cell absorptions and reflections by subtraction of a reference spectrum, taken with the cell filled with hydrocarbon free air. For each spectrum, a baseline zero was established by interpolation of a straight line between the average absorption in the following two regions: (i) 3.0–3.1 µm, and (ii) 3.9–4 µm. These regions were chosen for their insignificant levels of absorption for natural gas. Baseline zero reference measurements, made using carefully selected filters in regions unaffected by gas absorption, are well-known in non-dispersive infrared gas detectors.

The measurement performance of two different interference filters was compared. The first was chosen according to the previous text, to have a transmission peak close to 3.267 µm (actually 3.266 µ) and a fwhm bandwidth of under 0.9% (actually 0.81%). The second was chosen so as to maximise the signal from methane, with a transmission peak at 3.324 µm that corresponded with the maximum available methane signal, and a fwhm bandwidth of 0.83%.

(All figures provided by the manufacturer, NDC Infrared Engineering, Maldon, Essex, UK.)

The transmission spectra of each of the two interference filters was measured separately using the FTIR spectrometer with the same configuration settings as before. The effect of using each filter to make a non-dispersive measurement of gas concentration was then evaluated as follows.

Working in the transmission domain, the transmission spectrum of one of the filters was multiplied by the transmission spectrum of one of the gas mixtures.

This gave a signal equivalent to the transmission spectrum when the filter and gas cell were placed in series in the optical path of the spectrometer. The total amount of light that would pass through the cell/filter in this circumstance was calculated by integrating the light transmission in a broad window from 3.0 to 3.7 µm. This gave a signal equivalent to that measured by a single non-dispersive gas detector whose spectral selection of the gas absorption was determined by the interference filter alone.

This analysis was repeated for every combination of each of the two filters and three gas mixtures, plus a methane control, over a range of concentrations covering the % LEL scale.

The synthesised signals, in arbitrary units, were larger when using the second interference filter than when using a first interference filter. A single calibration factor was therefore applied to all the data obtained using each interference filter. This factor was chosen so as to give accurate results for the methane control gas at high concentrations.

Experimental Results

At a range of gas concentrations, the signals obtained for the different gas mixtures as set out in Table 1 when using each of the two interference filters are shown in FIGS. 4a and 4b.

A degree of nonlinearity can be observed in the results in FIGS. 4a and 4b, as a consequence of saturation effects associated with Beer's Law at high absorption levels. The degree of nonlinearity is greater in FIG. 4b, which is consistent with the second interference filter selecting a range of absorption lines with greater levels of absorption. Such nonlinearities can be reduced by using a calibration look-up table or by using a shorter optical pathlength through the gas cell.

It is clear from FIGS. 4a and 4b that use of the first interference filter at 3.266 µm (FIG. 4a) has resulted in a small spread of results for different gas mixtures at the same concentration. In contrast, the spread of results found when using the second interference filter (FIG. 4b) is much greater. When using gas detectors to quantify natural gas leaks, the composition of natural gas, to a degree represented by the above data, is not known. If calibrated using a methane only reference, a gas detector based on the second filter could overestimate the level of natural gas in real gas leaks by up to 100% because of inappropriate cross-sensitivity to the non-methane components of the natural gas.

The range of proportional errors associated with each filter was calculated for each gas concentration used. The average error range for the first interference filter was 10%, while that for the second filter was 36%. Even if methane is excluded from the analysis, the mean error range with the first filter is 5% compared to 19% with the second. It is clear that an appropriately chosen filter can significantly reduce the level of composition-related error for gas detectors based on non-dispersive infrared measurements.

The invention claimed is:

1. A method for determining the safety of a gas mixture including first and second flammable components together with a diluent gas, comprising:
performing infrared spectroscopy of the gas mixture using a filter having a peak transmission wavelength and a bandwidth to provide an output indicative of a percentage of the lower explosion limit (LEL) of the gas mixture within a predetermined tolerance of the output; and
selecting a filter in which the peak transmission wavelength and the band width of the filter, when viewed through said filter, are such that a first intensity of transmission through a gas mixture containing 50% of a LEL of said first flammable component is equal to a second intensity of transmission through a gas mixture containing 50% of a LEL of said second flammable component, within a 30% intensity tolerance.

2. The method according to claim 1, wherein said determining comprises:
selecting a filter such that a first rate of change of the first intensity of transmission $\partial I_1/\partial \lambda$ through a gas mixture containing 50% of the LEL of said first flammable component is equal to a second rate of change of the second intensity of transmission $\partial I_2/\partial \lambda$ through a gas mixture containing 50% of the LEL of said second flammable component, within a tolerance of 100 I/μm.

3. The method according to claim 1, wherein said determining comprises:
selecting a filter such that the first intensity for the first flammable component is selected for methane.

4. The method according to claim 3, wherein said determining comprises:
selecting a filter such that the second intensity for the second flammable component is selected for at least one of ethane, propane and or mixtures thereof.

5. The method according to any one of claims 1–4, further comprising:
producing a signal indicative of the % LEL for the mixture, within ±3% of the output.

6. An apparatus for determining the safety of a gas mixture including first and second flammable components together with a diluent gas, the apparatus comprising:
a gas region configured to receive a gas to be examined;
an infrared light source positioned to direct infrared light through said region;
a sensor configured to measure the intensity of light passed through said region; and
a filter positioned in a light path between said source and said sensor,
wherein said filter has a peak transmission wavelength and a bandwidth to provide an output indicative of a percentage of the lower explosion limit (LEL) of the gas mixture, and
the peak transmission wavelength and the band width of the filter are such that, when viewed through said filter, a first intensity of transmission through a gas mixture containing 50% of a LEL of said first flammable component is equal to a second intensity of transmission through a gas mixture containing 50% of a LEL of said second flammable component, within a 30% intensity tolerance.

7. The apparatus according to claim 6, wherein the gas region comprises:
a gas cell configured to contain a sample of the gas to be examined.

8. The apparatus according to claim 6, wherein the gas region comprises:
an open optical path through which the gas to be examined can flow.

9. The apparatus according to claim 6, wherein the filter comprises:
a gas correlation filter including a known mixture of said first and second flammable components together with the diluent gas to provide said sensor with an output indicative of the percentage of LEL of the gas mixture, within a predetermined tolerance of the output.

10. The apparatus according to claim 6, wherein, at the peak transmission wavelength of the filter, a first rate of change of intensity with increasing wavelength $\partial I_1/\partial \lambda$ for the gas mixture containing 50% of the LEL of said first component is equal to a second rate of change of intensity with increasing wavelength $\partial I_2/\partial \lambda$ for the gas mixture containing 50% of the LEL of said second component, within a tolerance of 100 I/μm.

11. A filter for use in the infrared spectroscopy of a gas mixture including methane as a first component and a second component selected from one of ethane, propane or mixtures thereof, together with a diluent gas, comprising:
said filter having a peak transmission wavelength and a bandwidth such that an output is provided, when an infrared light source having a flat wavelength distribution is used, indicative of a percentage of the lower explosion limit (LEL) of the gas mixture, within a predetermined tolerance of the outputs,
wherein the peak transmission wavelength and the band width of the filter are such that, when viewed through said filter, a first intensity of transmission through a gas mixture containing 50% of a LEL of said first component is equal to a second intensity of transmission through a gas mixture containing 50% of a LEL of said second component, within a 30% intensity tolerance.

12. The filter according to claim 11, wherein said filter has a peak transmission wavelength $\lambda_{max}$ from 3.265 to 3.269 μm.

13. The filter according to claim 12, wherein said filter has a band width, expressed in terms of a full width at half maximum, of less than 0.9% $\lambda_{max}$.

14. The filter according to claim 11, wherein said filter has a peak transmission wavelength $\lambda_{max}$ from 3.31 to 3.32 μm.

15. The filter according to claim 14, wherein said filter has a band width, expressed in terms of a full width at half maximum, of less than 0.7% $\lambda_{max}$.

16. The filter according to claim 11, wherein said filter has a peak transmission wavelength $\lambda_{max}$ from 1.673 to 1.675 μm.

17. The filter according to claim 16, wherein said filter has a band width, expressed in terms of a full width at half maximum, of between 0.5% and 6% $\lambda_{max}$.

18. A combination of an infrared light source and a filter for use in the infrared spectroscopy of a gas mixture including methane as a first component and a second component selected from ethane, propane, or mixtures thereof together with a diluent gas, comprising:
said filter having a peak transmission wavelength and a bandwidth such that an output is provided when said light source is used indicative of a percentage of the lower explosion limit (LEL) of the gas mixture, within a predetermined tolerance,
wherein the peak transmission wavelength and the band width of the filter, when viewed through said filter, are such that a first intensity of transmission through a gas mixture containing 50% of a LEL of said first flammable component is equal to a second intensity of transmission through a gas mixture containing 50% of a LEL of said second flammable component, within a 30% intensity tolerance.

19. A gas correlation filter for use in the infrared spectroscopy of natural gas, said filter comprising:
a mixture of methane and a second flammable component selected from ethane, propane or a mixture thereof, together with a diluent gas, in quantities that give equal signals from a mixture of methane/air at 50% of the lower explosion limit (LEL) and from a mixture of the second flammable component and air at 50% of the LEL, within a tolerance of 10% of the signal.

\* \* \* \* \*